United States Patent
Amemiya

(10) Patent No.: US 7,993,056 B2
(45) Date of Patent: Aug. 9, 2011

(54) ULTRASONIC PROBE AND ULTRASONIC DIAGNOSTIC APPARATUS

(75) Inventor: Shinichi Amemiya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 691 days.

(21) Appl. No.: 12/163,148

(22) Filed: Jun. 27, 2008

(65) Prior Publication Data

US 2009/0213897 A1 Aug. 27, 2009

(30) Foreign Application Priority Data

Jun. 29, 2007 (JP) ................................. 2007-171319

(51) Int. Cl.
*G01K 11/22* (2006.01)

(52) U.S. Cl. ...................................................... 374/117

(58) Field of Classification Search .................... 374/29, 374/43, 44, 117, 118, 119, 208

See application file for complete search history.

(56) References Cited

U.S. PATENT DOCUMENTS

| | | | |
|---|---|---|---|
| 4,201,087 A * | 5/1980 | Akita et al. ..................... | 374/119 |
| 4,650,346 A | 3/1987 | Tehon | |
| 4,817,615 A | 4/1989 | Fukukita et al. | |
| 5,158,087 A | 10/1992 | Gatzke | |
| 5,560,362 A | 10/1996 | Sliwa, Jr. et al. | |
| 5,776,065 A | 7/1998 | Mehmanpazir et al. | |
| 5,873,830 A | 2/1999 | Hossack et al. | |
| 6,201,900 B1 | 3/2001 | Hossack et al. | |
| 6,314,380 B1 | 11/2001 | Seip et al. | |
| 6,338,716 B1 | 1/2002 | Hossack et al. | |
| 6,470,286 B1 | 10/2002 | Seip et al. | |
| 7,142,114 B2 * | 11/2006 | Crowley ........................ | 600/549 |
| 7,156,551 B2 | 1/2007 | Ramamurthy et al. | |
| 7,284,904 B2 * | 10/2007 | Tokita et al. ..................... | 374/44 |
| 7,303,530 B2 | 12/2007 | Barnes et al. | |
| 2003/0204141 A1 | 10/2003 | Nock et al. | |
| 2004/0073113 A1 | 4/2004 | Salgo et al. | |
| 2005/0070811 A1* | 3/2005 | Crowley ........................ | 374/100 |
| 2006/0079815 A1* | 4/2006 | Sato et al. ..................... | 600/439 |
| 2006/0264730 A1* | 11/2006 | Stivoric et al. ................ | 600/549 |
| 2008/0194983 A1* | 8/2008 | Laurence et al. ............. | 600/549 |
| 2009/0036779 A1* | 2/2009 | Fukuda et al. ................ | 600/459 |
| 2011/0020787 A1* | 1/2011 | Lee ............................... | 600/309 |
| 2011/0046479 A1* | 2/2011 | Imran et al. ................... | 600/424 |

FOREIGN PATENT DOCUMENTS

| | | |
|---|---|---|
| JP | 08-056942 | 3/1996 |
| JP | 2003-125122 | 4/2003 |
| JP | 2007-065490 | 3/2007 |

* cited by examiner

*Primary Examiner* — G. Bradley Bennett
(74) *Attorney, Agent, or Firm* — Armstrong Teasdale LLP

(57) ABSTRACT

An ultrasonic diagnostic apparatus includes: an ultrasonic probe in which a first temperature sensor and a second temperature sensor are located posterior to an oscillator; and a surface temperature calculation device for calculating a surface temperature of the ultrasonic probe on the basis of a first detection temperature Ta detected by the first temperature sensor and a second detection temperature Tb detected by the second temperature sensor. Also, an ultrasonic diagnostic apparatus includes: an ultrasonic probe in which a first temperature sensor and a second temperature sensor are embedded in a backing material; and a surface temperature calculation device for calculating a surface temperature Ts of the ultrasonic probe on the basis of a first detection temperature Ta detected by the first temperature sensor and a second detection temperature Tb detected by the second temperature sensor.

20 Claims, 2 Drawing Sheets

ULTRASONIC PROBE AND ULTRASONIC DIAGNOSTIC APPARATUS

CROSS REFERENCE TO RELATED APPLICATIONS

This application claims the benefit of Japanese Patent Application No. 2007-171319 filed Jun. 29, 2007.

BACKGROUND OF THE INVENTION

The subject matter disclosed herein relates to an ultrasonic probe, an ultrasonic diagnostic apparatus, and a surface temperature estimating method for the ultrasonic probe, and more particularly to an ultrasonic probe, an ultrasonic diagnostic apparatus, and a surface temperature estimating method for the ultrasonic probe, which is capable of preventing an image from being deteriorated by acoustic disturbance that is caused by a temperature sensor, and also is capable of precisely estimating the surface temperature of the ultrasonic probe.

Up to now, there has been known an ultrasonic diagnostic apparatus in which a temperature sensor is disposed on a member that comes in contact with an object to be detected of the ultrasonic probe (for example, refer to Japanese Unexamined Patent Publication No. 2005-253776).

Also, there has been known an ultrasonic diagnostic apparatus in which plural temperature sensors are disposed at plural portions on the oscillator of the ultrasonic probe (for example, refer to Japanese Unexamined Patent Publication No. Hei 8 (1996)-56942).

Further, there has been known an ultrasonic diagnostic apparatus having a temperature sensor that detects the temperature of oil that is sealed in the interior of the ultrasonic probe (for example, refer to Japanese Unexamined Patent Publication No. 2001-321377).

In one of the above conventional ultrasonic diagnostic apparatuses in which a temperature sensor is disposed in the vicinity of the surface of the ultrasonic probe, there arises such a problem that an image is deteriorated by acoustic disturbance that is caused by a temperature sensor.

Also, in one of the above conventional ultrasonic diagnostic apparatuses in which the temperature sensor is disposed away from the surface of the ultrasonic probe, there arises such a problem that the surface temperature of the ultrasonic probe cannot be accurately known.

BRIEF DESCRIPTION OF THE INVENTION

It is desirable that the problems described previously are solved.

According to a first aspect of the invention, there is provided an ultrasonic probe in which a first temperature sensor and a second temperature sensor are located posterior to an oscillator.

In the ultrasonic probe according to the first aspect, since the temperature sensors are located posterior to the oscillator, it is possible to prevent an image from being deteriorated by acoustic disturbance that is caused by the temperature sensors. Also, since at least two temperature sensors are disposed, it is possible to precisely estimate the surface temperature of the ultrasonic probe on the basis of the detected temperature.

According to a second aspect of the invention, there is provided an ultrasonic probe in which a first temperature sensor and a second temperature sensor are embedded in a backing material.

In the ultrasonic probe according to the second aspect, since the temperature sensors are embedded in the backing material, it is possible to prevent an image from being deteriorated by acoustic disturbance that is caused by the temperature sensors. Also, since at least two temperature sensors are disposed, it is possible to precisely estimate the surface temperature of the ultrasonic probe on the basis of the detected temperature.

According to a third aspect of the invention, there is provided the ultrasonic probe according to the second aspect in which the first temperature sensor is positioned at a first point on a central axis of the backing material, and the second temperature sensor is positioned at a second point farther from a surface of the ultrasonic probe than the first point on the central axis.

In the ultrasonic probe according to the third aspect, since at least two temperature sensors are positioned on the central axis of the backing material, it is easy to estimate the highest temperature of the surface of the ultrasonic probe (the surface of the ultrasonic probe corresponding to the extension of the central axis of the backing material becomes the highest temperature).

According to a fourth aspect of the invention, there is provided an ultrasonic diagnostic apparatus, including: an ultrasonic probe in which a first temperature sensor and a second temperature sensor are located posterior to an oscillator; and a surface temperature calculation device for calculating a surface temperature of the ultrasonic probe on the basis of a first detection temperature Ta detected by the first temperature sensor and a second detection temperature Tb detected by the second temperature sensor.

In the ultrasonic diagnostic apparatus according to the fourth aspect, since the temperature sensors are located posterior to the oscillator of the ultrasonic probe, it is possible to prevent an image from being deteriorated by acoustic disturbance that is caused by the temperature sensors. Also, since the surface temperature Ts of the ultrasonic probe is calculated on the basis of the temperatures that have been detected by at least two temperature sensors, it is possible to precisely estimate the surface temperature.

According to a fifth aspect of the invention, there is provided an ultrasonic diagnostic apparatus, including: an ultrasonic probe in which a first temperature sensor and a second temperature sensor are embedded in a backing material; and a surface temperature calculation device for calculating a surface temperature Ts of the ultrasonic probe on the basis of a first detection temperature Ta detected by the first temperature sensor and a second detection temperature Tb detected by the second temperature sensor.

In the ultrasonic diagnostic apparatus according to the fifth aspect, since the temperature sensors are embedded in the backing material of the ultrasonic probe, it is possible to prevent an image from being deteriorated by acoustic disturbance that is caused by the temperature sensors. Also, since the surface temperature Ts of the ultrasonic probe is calculated on the basis of the temperatures that have been detected by at least two temperature sensors, it is possible to precisely estimate the surface temperature.

According to a sixth aspect of the invention, there is provided the ultrasonic diagnostic apparatus according to the fifth aspect, wherein the first temperature sensor is positioned at a first point on a central axis of the backing material, and the second temperature sensor is positioned at a second point farther from a surface of the ultrasonic probe than the first point on the central axis.

In the ultrasonic diagnostic apparatus according to the sixth aspect, since at least two temperature sensors are positioned on the central axis of the backing material of the ultrasonic probe, it is easy to estimate the highest temperature of the surface of the ultrasonic probe (the surface of the ultrasonic probe corresponding to the extension of the central axis of the backing material becomes the highest temperature).

According to a seventh aspect of the invention, there is provided the ultrasonic diagnostic apparatus according to any one of fourth to sixth aspects, wherein when it is assumed that a thermal resistance between the surface of the ultrasonic probe and the first temperature sensor is Ra, and a thermal resistance between the first temperature sensor and the second temperature sensor is Rb, the surface temperature calculation device calculates the surface temperature Ts by the following expression:

$$Ts=Ta+(Ta-Tb)Ra/Rb.$$

In the ultrasonic diagnostic apparatus according to the seventh aspect, in the case where the temperature change of the surface of the ultrasonic probe, the first sensor, and the second sensor can be linear, it is possible to simply calculate the surface of the ultrasonic probe.

According to an eighth aspect of the invention, there is provided an ultrasonic diagnostic apparatus, including: an ultrasonic probe in which a first temperature sensor and a second temperature sensor are located posterior to an oscillator; an external temperature sensor that detects an external temperature Te; and surface temperature calculation device for calculating a surface temperature Ts of the ultrasonic probe on the basis of a first detection temperature Ta detected by the first temperature sensor, a second detection temperature Tb detected by the second temperature sensor, and the external temperature Te.

In the above configuration, "external" means an environment in which the ultrasonic probe is located.

In the ultrasonic diagnostic apparatus according to the eighth aspect, since the temperature sensors are located posterior to the oscillator of the ultrasonic probe, it is possible to prevent an image from being deteriorated by acoustic disturbance that is caused by the temperature sensors. Also, since the surface temperature Ts of the ultrasonic probe is calculated on the basis of the temperatures that have been detected by at least two temperature sensors and the external temperature, it is possible to precisely estimate the surface temperature.

According to a ninth aspect of the invention, there is provided an ultrasonic diagnostic apparatus, including: an ultrasonic probe in which a first temperature sensor and a second temperature sensor are embedded in a backing material; an external temperature sensor that detects an external temperature Te; and a surface temperature calculation device for calculating a surface temperature Ts of the ultrasonic probe on the basis of a first detection temperature Ta detected by the first temperature sensor, a second detection temperature Tb detected by the second temperature sensor, and the external temperature Te.

In the above configuration, "external" means an environment in which the ultrasonic probe is located.

In the ultrasonic diagnostic apparatus according to the ninth aspect, since the temperature sensors are embedded in the backing material of the ultrasonic probe, it is possible to prevent an image from being deteriorated by acoustic disturbance that is caused by the temperature sensors. Also, since the surface temperature Ts of the ultrasonic probe is calculated on the basis of the temperatures that have been detected by at least two temperature sensors and the external temperature, it is possible to precisely estimate the surface temperature.

According to a tenth aspect of the invention, there is provided the ultrasonic diagnostic apparatus according to the ninth aspect, wherein the first temperature sensor is positioned at a first point on a central axis of the backing material, and the second temperature sensor is positioned at a second point farther from a surface of the ultrasonic probe than the first point on the central axis.

In the ultrasonic diagnostic apparatus according to the tenth aspect, since at least two temperature sensors are positioned on the central axis of the backing material of the ultrasonic probe, it is easy to estimate the highest temperature of the surface of the ultrasonic probe (the surface of the ultrasonic probe corresponding to the extension of the central axis of the backing material becomes the highest temperature).

According to an eleventh aspect of the invention, there is provided the ultrasonic diagnostic apparatus according to any one of the eighth to tenth aspects, wherein when it is assumed that a thermal resistance between the surface of the ultrasonic probe and the first temperature sensor is Ra, a thermal resistance between the first temperature sensor and the second temperature sensor is Rb, and a thermal resistance between the first temperature sensor and the outside is Re, the surface temperature calculation device calculates the surface temperature Ts by the following expression:

$$Ts=Ta+(Ta-Tb)Ra/Rb+(Ta-Te)Ra/Re.$$

In the ultrasonic diagnostic apparatus according to the eleventh aspect, in the case where the temperature change between the surface of the ultrasonic probe and the first temperature sensor, the temperature change between the first temperature sensor and the second temperature sensor, and the temperature change between the first temperature sensor and the outside can be linear, it is possible to simply calculate the surface of the ultrasonic probe.

According to a twelfth aspect of the invention, there is provided a surface temperature estimating method for an ultrasonic probe, including the steps of: locating a first temperature sensor and a second temperature sensor posterior to an oscillator of the ultrasonic probe; detecting a first detection temperature Ta by the first temperature sensor; detecting a second detection temperature Tb by the second temperature sensor; and calculating a surface temperature Ts of the ultrasonic probe on the basis of the first detection temperature Ta and the second detection temperature Tb.

In the surface temperature estimating method for an ultrasonic probe according to the twelfth aspect, since the temperature sensors are located posterior to the oscillator of the ultrasonic probe, it is possible to prevent an image from being deteriorated by acoustic disturbance that is caused by the temperature sensors. Also, since the surface temperature of the ultrasonic probe is estimated on the basis of the temperatures that have been detected by at least two temperature sensors, it is possible to precisely estimate the surface temperature.

According to a thirteenth aspect of the invention, there is provided a surface temperature estimating method for an ultrasonic probe, including the steps of: embedding a first temperature sensor and a second temperature sensor in a backing material of the ultrasonic probe; detecting a first detection temperature Ta by the first temperature sensor; detecting a second detection temperature Tb by the second temperature sensor; and calculating a surface temperature Ts of the ultrasonic probe on the basis of the first detection temperature Ta and the second detection temperature Tb.

In the surface temperature estimating method for an ultrasonic probe according to the thirteenth aspect, since the temperature sensors are embedded in the backing material, it is possible to prevent an image from being deteriorated by acoustic disturbance that is caused by the temperature sensors. Also, since the surface temperature of the ultrasonic probe is estimated on the basis of the temperatures that have been detected by at least two temperature sensors, it is possible to precisely estimate the surface temperature.

According to a fourteenth aspect of the invention, there is provided the surface temperature estimating method for an ultrasonic probe according to the thirteenth aspect, wherein the first temperature sensor is positioned at a first point on a central axis of the backing material, and the second temperature sensor is positioned at a second point farther from a surface of the ultrasonic probe than the first point on the central axis.

In the surface temperature estimating method for an ultrasonic probe according to the fourteenth aspect, since at least two temperature sensors are positioned on the central axis of the backing material of the ultrasonic probe, it is easy to estimate the highest temperature of the surface of the ultrasonic probe (the surface of the ultrasonic probe corresponding to the extension of the central axis of the backing material becomes the highest temperature).

According to a fifteenth aspect of the invention, there is provided the surface temperature estimating method for an ultrasonic probe according to any one of twelfth to fourteenth aspects, wherein when it is assumed that a thermal resistance between the surface of the ultrasonic probe and the first temperature sensor is Ra, and a thermal resistance between the first temperature sensor and the second temperature sensor is Rb, the surface temperature Ts is calculated by the following expression:

$$Ts=Ta+(Ta-Tb)Ra/Rb.$$

In the surface temperature estimating method for an ultrasonic probe according to the fifteenth aspect, in the case where the temperature change of the surface of the ultrasonic probe, the first temperature sensor, and the second temperature sensor can be linear, it is possible to simply calculate the surface of the ultrasonic probe.

According to a sixteenth aspect of the invention, there is provided the surface temperature estimating method for an ultrasonic probe according to any one of the twelfth to fourteenth aspects, wherein a temperature change function is obtained from the results of measuring the first detection temperature Ta, the second detection temperature Tb, and the surface temperature Ts, and the surface temperature Ts of the ultrasonic probe is calculated by using the first detection temperature Ta, the second detection temperature Tb, and the temperature change function.

In the ultrasonic diagnostic apparatus according to the sixteenth aspect, the temperature change function is obtained from the temperature measured result, and the surface temperature of the ultrasonic probe is estimated by using the determined temperature change function. As a result, it is possible to precisely estimate the surface temperature.

According to a seventeenth aspect of the invention, there is provided a surface temperature estimating method for an ultrasonic probe, including the steps of: locating a first temperature sensor and a second temperature sensor posterior to an oscillator of the ultrasonic probe; detecting a first detection temperature Ta by the first temperature sensor; detecting a second detection temperature Tb by the second temperature sensor; detecting an external temperature Te; and calculating a surface temperature Ts of the ultrasonic probe on the basis of the first detection temperature Ta, the second detection temperature Tb, and the external temperature Te.

In the above configuration, "external" means an environment in which the ultrasonic probe is located.

In the surface temperature estimating method for an ultrasonic probe according to the seventeenth aspect, since the temperature sensors are located posterior to the oscillator of the ultrasonic probe, it is possible to prevent an image from being deteriorated by acoustic disturbance that is caused by the temperature sensors. Also, since the surface temperature Ts of the ultrasonic probe is calculated on the basis of the temperatures that have been detected by at least two temperature sensors and the external temperature, it is possible to precisely estimate the surface temperature.

According to an eighteenth aspect of the invention, there is provided a surface temperature estimating method for an ultrasonic probe, including the steps of: embedding a first temperature sensor and a second temperature sensor posterior in a backing material of the ultrasonic probe; detecting a first detection temperature Ta by the first temperature sensor; detecting a second detection temperature Tb by the second temperature sensor; detecting an external temperature Te; and calculating a surface temperature Ts of the ultrasonic probe on the basis of the first detection temperature Ta, the second detection temperature Tb, and the external temperature Te.

In the above configuration, "external" means an environment in which the ultrasonic probe is located.

In the surface temperature estimating method for an ultrasonic probe according to the eighteenth aspect, since the temperature sensors are embedded in the backing material of the ultrasonic probe, it is possible to prevent an image from being deteriorated by acoustic disturbance that is caused by the temperature sensors. Also, since the surface temperature Ts of the ultrasonic probe is calculated on the basis of the temperatures that have been detected by at least two temperature sensors and the external temperature, it is possible to precisely estimate the surface temperature.

According to a nineteenth aspect of the invention, there is provided the surface temperature estimating method for an ultrasonic probe according to the eighteen aspect, wherein the first temperature sensor is positioned at a first point on a central axis of the backing material, and the second temperature sensor is positioned at a second point farther from a surface of the ultrasonic probe than the first point on the central axis.

In the surface temperature estimating method for an ultrasonic probe according to the nineteenth aspect, since at least two temperature sensors are positioned on the central axis of the backing material of the ultrasonic probe, it is easy to estimate the highest temperature of the surface of the ultrasonic probe (the surface of the ultrasonic probe corresponding to the extension of the central axis of the backing material becomes the highest temperature).

According to a twentieth aspect of the invention, there is provided a surface temperature estimating method for an ultrasonic probe according to any one of the seventeenth to nineteenth aspects, wherein when it is assumed that a thermal resistance between the surface of the ultrasonic probe and the first temperature sensor is Ra, a thermal resistance between the first temperature sensor and the second temperature sensor is Rb, and a thermal resistance between the first temperature sensor and the outside is Re, the surface temperature Ts is calculated by the following expression:

$$Ts=Ta+(Ta-Tb)Ra/Rb+(Ta-Te)Ra/Re.$$

In the surface temperature estimating method for an ultrasonic probe according to the twentieth aspect, in the case where the temperature change between the surface of the ultrasonic probe and the first temperature sensor, the temperature change between the first temperature sensor and the second temperature sensor, and the temperature change between the first temperature sensor and the outside can be linear, it is possible to simply calculate the surface of the ultrasonic probe.

According to a twenty-first aspect of the invention, there is provided the surface temperature estimating method for an ultrasonic probe according to any one of seventeenth to nineteenth aspects, wherein a temperature change function is obtained from the results of measuring the first detection temperature Ta, the second detection temperature Tb, the external temperature Te, and the surface temperature Ts, and the surface temperature Ts of the ultrasonic probe is calculated by using the first detection temperature Ta, the second detection temperature Tb, the external temperature Te, and the temperature change function.

In the ultrasonic diagnostic apparatus according to the twenty-first aspect, the temperature change function is obtained from the temperature measured result, and the surface temperature of the ultrasonic probe is estimated by using the determined temperature change function. As a result, it is possible to precisely estimate the surface temperature.

According to the ultrasonic probe, the ultrasonic diagnostic apparatus, and the surface temperature estimating method for the ultrasonic probe of the invention, it is possible to prevent an image from being deteriorated by acoustic disturbance that is caused by the temperature sensors. Also, it is possible to precisely estimate the surface temperature of the ultrasonic probe.

The ultrasonic probe, the ultrasonic diagnostic apparatus, and the surface temperature estimating method for the ultrasonic probe according to the invention can be used in estimating the surface temperature of the ultrasonic diagnostic apparatus in use.

Further objects and advantages of the present invention will be apparent from the following description of the preferred embodiments of the invention as illustrated in the accompanying drawings.

DETAILED DESCRIPTION OF THE INVENTION

Hereinafter, a description will be given in more detail of preferred embodiments of the invention with reference to the drawings. The invention is not limited by the embodiments.

Figure 1:
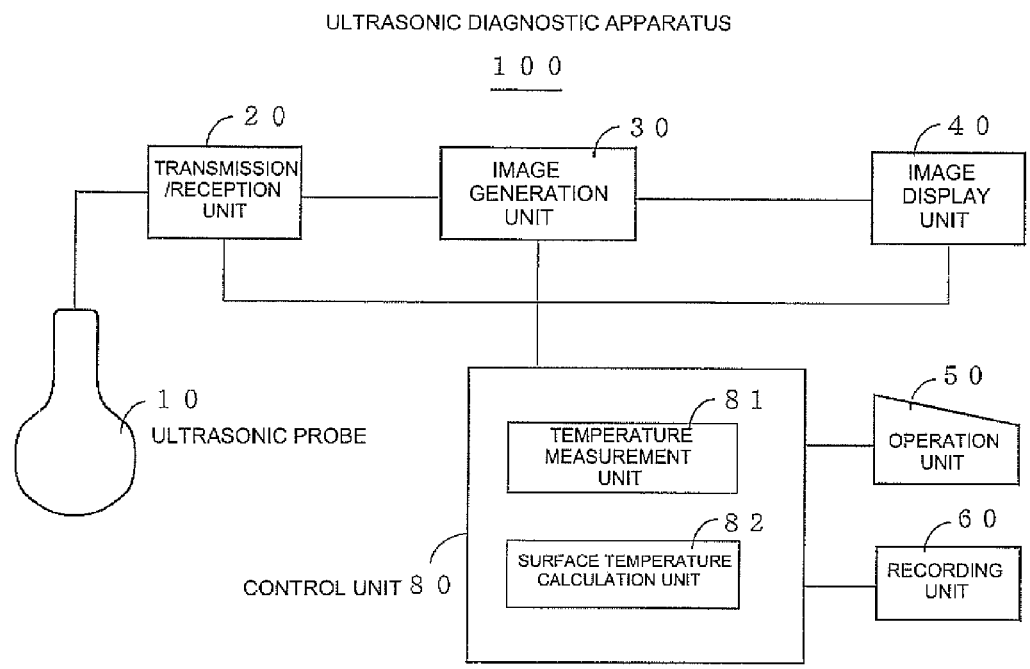
FIG. 1 is a block diagram showing an ultrasonic diagnostic apparatus according to a first embodiment.

FIG. 1 is a block diagram showing the configuration of an ultrasonic diagnostic apparatus 100 according to a first embodiment.

The ultrasonic diagnostic apparatus 100 includes an ultrasonic probe 10, a transmission/reception unit 20 that drives the ultrasonic probe 10 and scans the interior of an body to be detected with an ultrasonic beam, and an image generating unit 30 that generates the ultrasonic image on the basis of the signal obtained by the transmission/reception unit 20, an image display unit 40 that displays the ultrasonic image, and an operation unit 50 for allowing an operator to give an instruction or data. The ultrasonic diagnostic apparatus 100 also includes a recording unit 60 that records the ultrasonic image, a control unit 80 that controls the entire system, and a temperature measurement unit 81 and a surface temperature calculation unit 82 that are included in the control unit 80.

Figure 2:
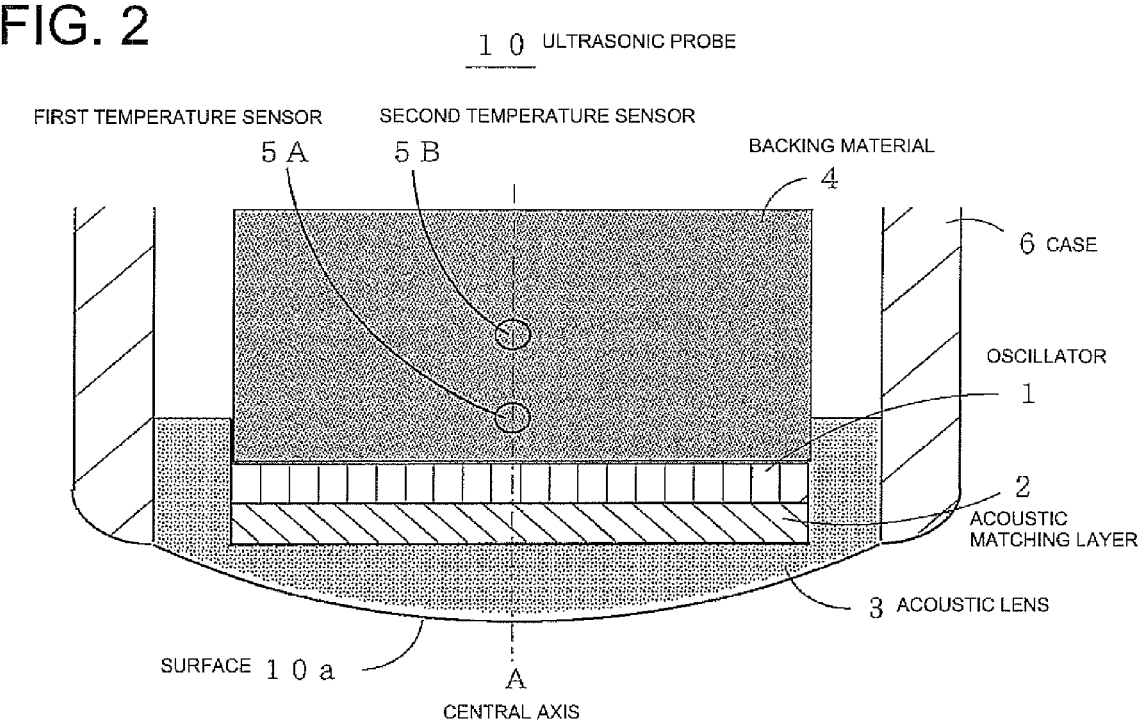
FIG. 2 is a partial cross-sectional view showing an ultrasonic probe according to the first embodiment.

FIG. 2 is a partially cross-sectional view showing the ultrasonic probe 10 according to the first embodiment.

The ultrasonic probe 10 is equipped with an oscillator 1, an acoustic matching layer 2, an acoustic lens 3, a backing material 4, a first temperature sensor 5A and a second sensor 5B that are embedded in the backing material 4, and a case 6.

A large number of oscillators 1 are arranged in the lateral direction of FIG. 2. Also, in the case where oscillator 1 is two-dimensionally arranged, the oscillators 1 are also arranged in a direction perpendicular to the lateral direction shown in FIG. 2.

The first temperature sensor 5A is positioned at a first point on the central axis A of the backing material 4. Also, the second temperature sensor 5B is positioned at a second point farther from a surface 10a of the ultrasonic probe 10 than the first point on the central axis A.

A temperature measurement unit 81 of the control unit 80 obtains the first detection temperature Ta by the first temperature sensor 5A, and also obtains the second detection temperature Tb by the second temperature sensor 5B.

When it is assumed that a thermal resistance between the surface 10a of the ultrasonic probe 10 and the first temperature sensor 5A is Ra, and a thermal resistance between the first temperature sensor 5A and the second temperature sensor 5B is Rb, the surface temperature calculation unit 82 of the control unit 80 calculates a surface temperature Ts by the following expression:

$$Ts = Ta + (Ta - Tb)Ra/Rb.$$

Figure 3:
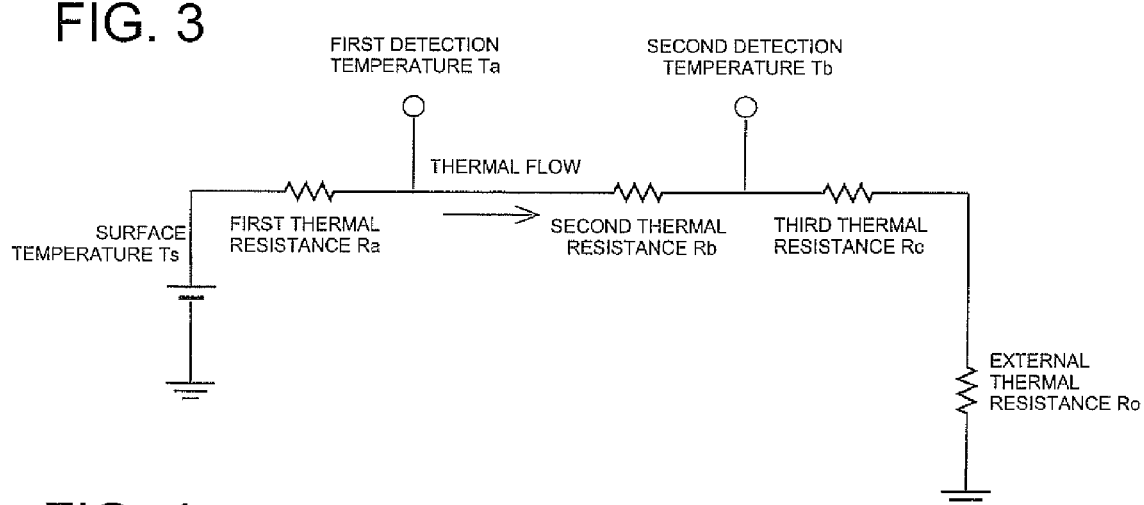
FIG. 3 is an equivalent thermal circuit diagram according to the first embodiment.

FIG. 3 is an equivalent thermal circuit in the case where the temperature change of the first detection temperature Ta and the second detection temperature Tb can be linear.

A calculation expression in the surface temperature calculation unit 82 can be obtained from the equivalent thermal circuit.

According to the ultrasonic probe 10 and the ultrasonic diagnostic apparatus 100 of the first embodiment, since the temperature sensors 5A and 5B are embedded in the backing material 4, it is possible to prevent an image from being deteriorated by acoustic disturbance that is caused by the temperature sensors 5A and 5B. Also, since the surface temperature Ts of the ultrasonic probe 10 is calculated on the basis of the temperature that have been detected by the two temperature sensors 5A and 5B, it is possible to precisely estimate the surface temperature Ts. Further, since two temperature sensors 5A and 5B are positioned on the central axis A of the backing material 4, it is easy to estimate the highest temperature of the surface 10a of the ultrasonic probe 10.

Figure 4:
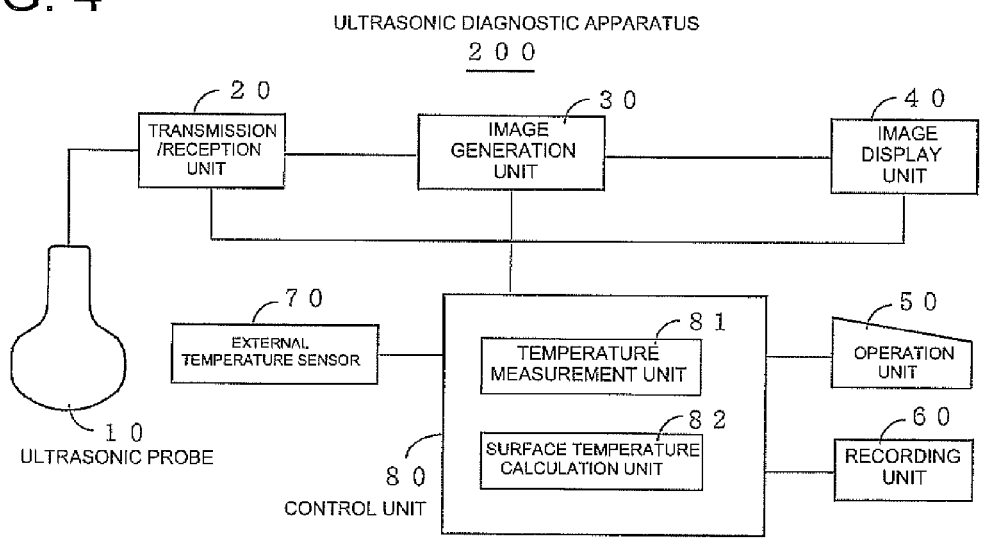
FIG. 4 is a block diagram showing an ultrasonic diagnostic apparatus according to a second embodiment.

FIG. 4 is a block diagram showing the configuration of an ultrasonic diagnostic apparatus 200 according to a second embodiment.

The ultrasonic diagnostic apparatus 200 is equipped with an ultrasonic probe 10, a transmission/reception unit 20 that drives the ultrasonic probe 10 and scans the interior of an object to be detected with an ultrasonic beam, an image generation unit 30 that generates an ultrasonic image on the basis of a signal that has been obtained by the transmission/ reception unit 20, and an image display unit 40 that displays the ultrasonic image. The ultrasonic diagnostic apparatus 200 also includes an operation unit 50 for allowing an operator to give an instruction or data, a recording unit 60 that records the ultrasonic image, an external temperature sensor 70 for detecting the external temperature, a control unit 80 that controls the entire system, and a temperature measurement unit 81 and a surface temperature calculation unit 82 which are included in the control unit 80.

The ultrasonic probe 10 is identical with that of the ultrasonic probe 10 of the first embodiment.

The temperature measurement unit 81 of the control unit 80 obtains the first detection temperature Ta from the first temperature sensor 5A, and obtains the second detection temperature Tb from the second temperature sensor 5B. Also, the temperature measurement unit 81 obtains the external temperature Te from the external temperature sensor 70.

When it is assumed that a thermal resistance between the surface 10*a* of the ultrasonic probe 10 and the first temperature sensor 5A is Ra, a thermal resistance between the first temperature sensor 5A and the second temperature sensor 5B is Rb, and a thermal resistance between the first temperature sensor 5A and the outside is Re, the surface temperature calculation unit 82 of the control unit 80 calculates the surface temperature Ts by the following expression:

$$Ts=Ta+(Ta-Tb)Ra/Rb+(Ta-Te)Ra/Re.$$

Figure 5:
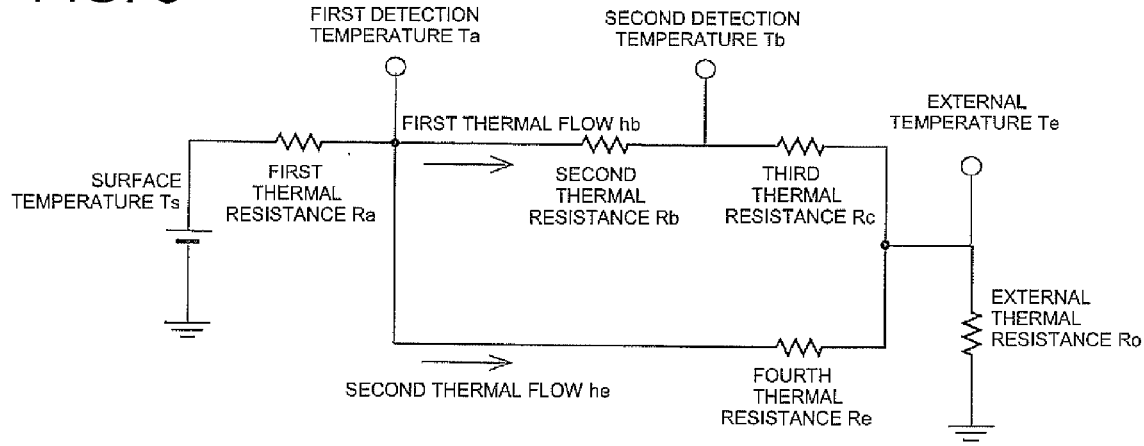
FIG. 5 is an equivalent thermal circuit diagram according to the second embodiment.

FIG. 5 is an equivalent thermal circuit in the case where the temperature change between the surface temperature Ts and the first detection temperate Ta, the temperature change between the first detection temperature Ta and the second detection temperature Tb, and the temperature change between the first detection temperature Ta and the external temperature Te can be linear, respectively.

A calculation expression in the surface temperature calculation unit 82 can be obtained from the equivalent thermal circuit.

According to the ultrasonic probe 110 and the ultrasonic diagnostic apparatus 200 of the second embodiment, since the temperature sensors 5A and 5B are embedded in the backing material 4, it is possible to prevent an image from being deteriorated by acoustic disturbance that is caused by the temperature sensors 5A and 5B. Also, since the surface temperature Ts of the ultrasonic probe 10 is calculated on the basis of the temperatures that have been detected by the three temperature sensors 5A, 5B, and 5*e*, it is possible to precisely estimate the surface temperature Ts. Further, since two temperature sensors 5A and 5B are positioned on the central axis A of the backing material 4, it is easy to estimate the highest temperature of the surface 10*a* of the ultrasonic probe 10.

Alternatively, it is possible that a temperature change function is determined according to the results of measuring the first detection temperature Ta, the second detection temperature Tb, and the surface temperature Ts, and the surface temperature Ts of the ultrasonic probe 10 is calculated by using the first detection temperature Ta, the second detection temperature Tb, and the temperature change function.

Also, it is possible that three or more temperature sensors are embedded in the backing material 4, and the temperature change function is obtained from the results of measuring the detection temperatures of those temperature sensors and the surface temperature Ts. Also, the surface temperature Ts of the ultrasonic probe 10 is calculated by using the detection temperatures of three or more temperature sensors and the temperature change function.

Alternatively, it is possible that a temperature change function is determined according to the results of measuring the first detection temperature Ta, the second detection temperature Tb, the external temperature Te, and the surface temperature Ts of the ultrasonic probe 10 is calculated by using the first detection temperature Ta, the second detection temperature Tb, the external temperature Te, and the temperature change function.

Also, it is possible that three or more temperature sensors are embedded in the backing material 4, and the temperature change function is obtained from the results of measuring the detection temperatures of those temperature sensors, the external temperature Te, and the surface temperature Ts. Also, the surface temperature Ts of the ultrasonic probe 10 is calculated by using the detection temperatures of three or more temperature sensors, the external temperature Te, and the temperature change function.

Alternatively, it is possible that the surface temperature Ts of the ultrasonic probe 10 can be calculated as in the same manner as that of the first to fourth embodiments with the use of the ultrasonic probe 10. In the ultrasonic probe 10, at least the first temperature sensor 5A and the second temperature sensor 5B are located at positions of different thermal resistances from the surface 10*a* of the ultrasonic probe 10 on a flexible substrate that is connected to the oscillator 1 of the ultrasonic probe 10.

The fifth embodiment is advantageous in that the manufacturing is facilitated.

Many widely different embodiments of the invention will be configured without departing from the spirit and the scope of the present invention. It should be understood that the present invention is not limited to the specific embodiments described in the specification, except as defined in the appended claims.

What is claimed is:

1. An ultrasonic probe comprising a first temperature sensor and a second temperature sensor located posterior to an oscillator.

2. An ultrasonic probe comprising a first temperature sensor and a second temperature sensor embedded in a backing material.

3. The ultrasonic probe according to claim 2, wherein said first temperature sensor is positioned at a first point on a central axis of said backing material, and said second temperature sensor is positioned at a second point further from a surface of said ultrasonic probe than the first point on the central axis.

4. An ultrasonic diagnostic apparatus, comprising:
an ultrasonic probe comprising a first temperature sensor and a second temperature sensor located posterior to an oscillator; and
a surface temperature calculation device configured to calculate a surface temperature of said ultrasonic probe based on a first detection temperature detected by said first temperature sensor and a second detection temperature detected by said second temperature sensor.

5. An ultrasonic diagnostic apparatus, comprising:
an ultrasonic probe comprising a first temperature sensor and a second temperature sensor embedded in a backing material; and
a surface temperature calculation device configured to calculate a surface temperature of said ultrasonic probe based on a first detection temperature detected by said first temperature sensor and a second detection temperature detected by said second temperature sensor.

6. The ultrasonic diagnostic apparatus according to claim 5, wherein said first temperature sensor is positioned at a first point on a central axis of said backing material, and said second temperature sensor is positioned at a second point further from a surface of said ultrasonic probe than the first point on the central axis.

7. The ultrasonic diagnostic apparatus according to claim 4, wherein said surface temperature calculation device is configured to calculate the surface temperature by the following expression:

$$Ts=Ta+(Ta-Tb)Ra/Rb$$

where the surface temperature is Ts, the first detection temperature is Ta, the second detection temperature is Tb, a thermal resistance between a surface of said ultrasonic probe and said first temperature sensor is Ra, and a thermal resistance between said first temperature sensor and said temperature sensor is Rb.

8. The ultrasonic diagnostic apparatus according to claim 5, wherein said surface temperature calculation device is configured to calculate the surface temperature by the following expression:

$$Ts=Ta+(Ta-Tb)Ra/Rb$$

where the surface temperature is Ts, the first detection temperature is Ta, the second detection temperature is Tb, a thermal resistance between a surface of said ultrasonic probe and said first temperature sensor is Ra, and a thermal resistance between said first temperature sensor and said temperature sensor is Rb.

9. The ultrasonic diagnostic apparatus according to claim 6, wherein said surface temperature calculation device is configured to calculate the surface temperature by the following expression:

$$Ts=Ta+(Ta-Tb)Ra/Rb$$

where the surface temperature is Ts, the first detection temperature is Ta, the second detection temperature is Tb, a thermal resistance between a surface of said ultrasonic probe and said first temperature sensor is Ra, and a thermal resistance between said first temperature sensor and said temperature sensor is Rb.

10. An ultrasonic diagnostic apparatus according to claim 4, further comprising an external temperature sensor configured to detect an external temperature, wherein said surface temperature calculation device is configured to calculate the surface temperature of said ultrasonic probe based on a first detection temperature detected by said first temperature sensor, a second detection temperature detected by said second temperature sensor, and the external temperature.

11. An ultrasonic diagnostic apparatus according to claim 5, further comprising an external temperature sensor configured to detect an external temperature, wherein said surface temperature calculation device is configured to calculate the surface temperature of said ultrasonic probe based on a first detection temperature detected by said first temperature sensor, a second detection temperature detected by said second temperature sensor, and the external temperature.

12. The ultrasonic diagnostic apparatus according to claim 11, wherein said first temperature sensor is positioned at a first point on a central axis of said backing material, and said second temperature sensor is positioned at a second point further from a surface of said ultrasonic probe than the first point on the central axis.

13. The ultrasonic diagnostic apparatus according to claim 10, wherein said surface temperature calculation device is configured to calculate the surface temperature by the following expression:

$$Ts=Ta+(Ta-Tb)Ra/Rb+(Ta-Te)Ra/Re$$

where the surface temperature is Ts, the first detection temperature is Ta, the second detection temperature is Tb, the external temperature is Te, a thermal resistance between the surface of said ultrasonic probe and said first temperature sensor is Ra, a thermal resistance between said first temperature sensor and said second temperature sensor is Rb, and a thermal resistance between said first temperature sensor and the outside is Re.

14. The ultrasonic diagnostic apparatus according to claim 11, wherein said surface temperature calculation device is configured to calculate the surface temperature by the following expression:

$$Ts=Ta+(Ta-Tb)Ra/Rb+(Ta-Te)Ra/Re$$

where the surface temperature is Ts, the first detection temperature is Ta, the second detection temperature is Tb, the external temperature is Te, a thermal resistance between the surface of said ultrasonic probe and said first temperature sensor is Ra, a thermal resistance between said first temperature sensor and said second temperature sensor is Rb, and a thermal resistance between said first temperature sensor and the outside is Re.

15. The ultrasonic diagnostic apparatus according to claim 12, wherein said surface temperature calculation device is configured to calculate the surface temperature by the following expression:

$$Ts=Ta+(Ta-Tb)Ra/Rb+(Ta-Te)Ra/Re$$

where the surface temperature is Ts, the first detection temperature is Ta, the second detection temperature is Tb, the external temperature is Te, a thermal resistance between the surface of said ultrasonic probe and said first temperature sensor is Ra, a thermal resistance between said first temperature sensor and said second temperature sensor is Rb, and a thermal resistance between said first temperature sensor and the outside is Re.

16. The ultrasonic probe according to claim 1, wherein said first temperature sensor and said second temperature sensor are embedded in a backing material.

17. The ultrasonic probe according to claim 1, further comprising an acoustic matching layer located anterior to said oscillator.

18. The ultrasonic probe according to claim 17, further comprising an acoustic lens located adjacent to said acoustic matching layer.

19. The ultrasonic probe according to claim 2, further comprising an oscillator, wherein said first temperature sensor and said second temperature sensor are located posterior to said oscillator.

20. The ultrasonic probe according to claim 19, further comprising an acoustic matching layer located anterior to said oscillator and posterior to an acoustic lens.

* * * * *